United States Patent
Pellegrino (10) Patent No.: US 7,263,170 B2
(45) Date of Patent: Aug. 28, 2007

(54) RADIATION THERAPY SYSTEM FEATURING ROTATABLE FILTER ASSEMBLY

(76) Inventor: Anthony J. Pellegrino, 23 Sunswept Dr., New Fairfield, CT (US) 06812

( * ) Notice: Subject to any disclaimer, the term of this patent is extended or adjusted under 35 U.S.C. 154(b) by 0 days.

(21) Appl. No.: 11/240,919

(22) Filed: Sep. 30, 2005

(65) Prior Publication Data
US 2007/0076851 A1 Apr. 5, 2007

(51) Int. Cl.
  G21K 3/00 (2006.01)
  H05G 1/58 (2006.01)
(52) U.S. Cl. .............. 378/158; 378/115; 378/156
(58) Field of Classification Search .............. 378/65, 378/115, 156–159; 600/1
See application file for complete search history.

(56) References Cited

U.S. PATENT DOCUMENTS

| | | | |
|---|---|---|---|
| 2,506,342 A | 5/1950 | Burke | |
| 3,999,073 A | 12/1976 | Hounsfield | |
| 4,277,685 A | 7/1981 | Covic | |
| 4,347,440 A * | 8/1982 | Haas | 378/156 |
| 4,399,550 A * | 8/1983 | Hauck et al. | 378/5 |
| 4,433,431 A * | 2/1984 | Pfeiler | 378/157 |
| 4,528,685 A | 7/1985 | Kump et al. | |
| 4,894,855 A | 1/1990 | Kresse | |
| 5,081,660 A | 1/1992 | Fujisaki | |
| 5,396,889 A * | 3/1995 | Ueda et al. | 600/407 |
| 5,835,555 A | 11/1998 | Barry | |
| 6,036,362 A * | 3/2000 | Schmitt | 378/206 |
| 6,325,537 B1 | 12/2001 | Watanabe | |
| 2003/0048875 A1 | 3/2003 | Mihara | |

OTHER PUBLICATIONS

"Therapax 150 Microprocessor-Controlled Superficial Radiation Treatment System" brochure by Pantak, Inc., 1996.
"D3150 Superficial X-Ray Therapy System" by Gulmay Medical, Document No. GM-1508-1, Issue Date: Nov. 2000.
"RT-100 Superficial and Endotherapy Apparatus" Product Data issued by N.V. Phillips' Glaelampenfabricken, Medical Systems divsision, Eindhoven Netherlands, Supercedes Product Data XK1025 dated X-'69.

* cited by examiner

Primary Examiner—Edward J. Glick
Assistant Examiner—Anastasia S. Midkiff (57) ABSTRACT

A radiation therapy system is provided having a radiation source for providing radiation for treating a patient, including treating skin cancer, wherein the radiation source features a filtering device that changes its filtering characteristic for filtering the radiation for treating the patient in response to a control signal. The filtering device includes two filters and a radiation blocker circumferentially arranged on a cylindrical member. The filtering characteristic is changed by rotating the filtering device in response to the control signal. The filtering device includes a driving unit for rotating the filtering device in response to the control signal in order to change its filtering characteristic, such as a motor with a gearing arrangement for coupling to a corresponding gearing arrangement on the filtering device. In this embodiment, the means for providing the radiation, i.e. the x-ray tube, is arranged inside the filtering device.

17 Claims, 11 Drawing Sheets

Figure 5: The Basic Circuitry

RADIATION THERAPY SYSTEM FEATURING ROTATABLE FILTER ASSEMBLY

BACKGROUND OF THE INVENTION

1. Field of the Invention

The present invention relates to a radiation system for treating patients with certain skin conditions, such as skin cancer; and more particularly, it relates to a low energy or superficial x-ray radiation therapy system equipped with x-ray filters for regulating the characteristics of the radiation.

2. Description of Related Art

The so-called superficial x-rays are low energy x-rays useful for treating certain conditions within a shallow depth of human skin, such as skin cancers and dermatological disorders. A superficial radiation therapy system delivers most of the radiation at or near the skin surface. Superficial radiation therapy is effective for certain patients with basal cell carcinoma, squamous cell carcinoma and Kaposi's sarcoma. These types of cancer can be disfiguring due to the location and surgical scarring. Superficial radiation treatment is simple, painless and significantly less expensive than other alternatives, and it does not leave scarring like surgery.

In superficial radiation therapy treatment, it is very important to insure that the patient receives the correct radiation energy and dose. Commercially available superficial x-ray therapy systems, such as PHILIPS RT.-100, THERAPAX 150 and GULMAY D3150, have an x-ray source with several adjustable energy (in kilovolts) and intensity (in milliamps) levels. For example the PHILIPS RT-100 has settings of 10/8, 20/10, 30/10, 37/10, 45/10, 55/10 70/10, 85/8, and 100/8 kV/mA.

The quality of the X-rays plays a great role in the size of the administered dose. Radiation from a x-ray tube normally has a broad energy spectrum. Higher energy radiation is useful in treating the patient, because it passes through the skin and reaches a certain depth. Lower energy radiation, by contrast, gets stopped near the skin surface. Therefore, it is primarily the low energy radiation that creates unnecessary exposure to the patient. For this reason, a filter, normally made with a metal like copper or aluminum, is placed in front of the X-ray tube. Some low energy radiation is absorbed in the filter plate, and the remaining radiation emerging from the filter has a narrower spectrum. This filtration can also regulate the radiation dose delivered to the patient. In existing superficial radiation treatment systems such as PHILIPS RT-100, there are as many as nine filters in varying materials and thickness, each is used for one particular voltage/current setting of the x-ray tube. A user (operator of the x-ray therapy system) sets up a filter according to the x-ray tube setting, by inserting the filter plate manually. Since an incorrect insertion of a filter could result in improper radiation energy and dose to be delivered to the patient, to prevent this problem, an interlocking mechanism is used in some systems. Once energy/current level is set, only the filter with the correct interlocking notches can be inserted.

In addition to the filters, the x-ray systems are equipped with an x-ray blocker that is a thick piece of heavy metal such as lead. The blocker is normally used during warm-up process of the x-ray tube in order to prevent x-rays from exiting the radiation head. In the existing systems, this blocker is also inserted manually.

What is needed is an automatic filter setting mechanism that selects correct filter (or filter combination) in correspondence to the voltage and current setting of the x-ray system and inserts such correct filter or lead blocker automatically by a command from a central controlling module, controlled by the system user.

SUMMARY OF THE INVENTION

In its broadest sense, the present invention provides a radiation therapy system having a radiation source for providing radiation for treating a patient, including treating skin cancer, wherein the radiation source features a filtering device that changes its filtering characteristic for filtering the radiation for treating the patient in response to a control signal. The whole thrust of the invention is to allow an operator of the radiation therapy system 100 to set and/or change automatically a filter setting without manually handling any filters in the radiation system.

In one embodiment according to the invention, the filtering device includes a rotatable filtering assembly having a cylindrical member with two filters and a radiation blocker circumferentially arranged thereon. The filtering characteristic is changed by rotating the filtering device in response to the control signal. The filtering device also includes a suitable driving unit for rotating the filtering assembly in response to the control signal in order to change its filtering characteristic, such as a motor with a gearing arrangement for coupling to a corresponding gearing arrangement on the filtering assembly. In this embodiment, the radiation source includes an x-ray source arranged in relation to the filtering assembly, including having its focal point focused inside the rotatable filtering assembly.

Moreover, the radiation therapy system also includes a processing module that can respond to an input provided by a user (the operator of the system), such an input contains information that is used to determine a filter setting, and that provides the control signal for changing filtering characteristics.

The radiation therapy system may also include a user input console for receiving the input provided by the user.

One advantage of the present invention is that it provides an automatic filter setting mechanism that selects the correct filter (or filter combination) in correspondence to the voltage and current setting of the X-ray system and rotates the filter assembly to the correct filter automatically in response to the control command or signal from the central controlling processing module, controlled by the system user. The central control and rotatable filter setting provides an important contribution to the state of the art of radiation treatment of patients.

BRIEF DESCRIPTION OF THE DRAWING

The above and other objects, features and advantages of the invention will become apparent from a consideration of the subsequent detailed description presented in connection with accompanying drawings, in which:

FIG. 3 includes FIGS. 3A and 3B, wherein FIG. 3A is a schematic partial view of the side of a radiation source of a radiation therapy system according to the present invention; and wherein

FIG. 4 includes FIGS. 4A and 4B, wherein FIG. 4A is a schematic view of the front of a rotatable filtering device according to the present invention; and wherein

BEST MODE FOR CARRYING OUT THE INVENTION

Figure 1A:
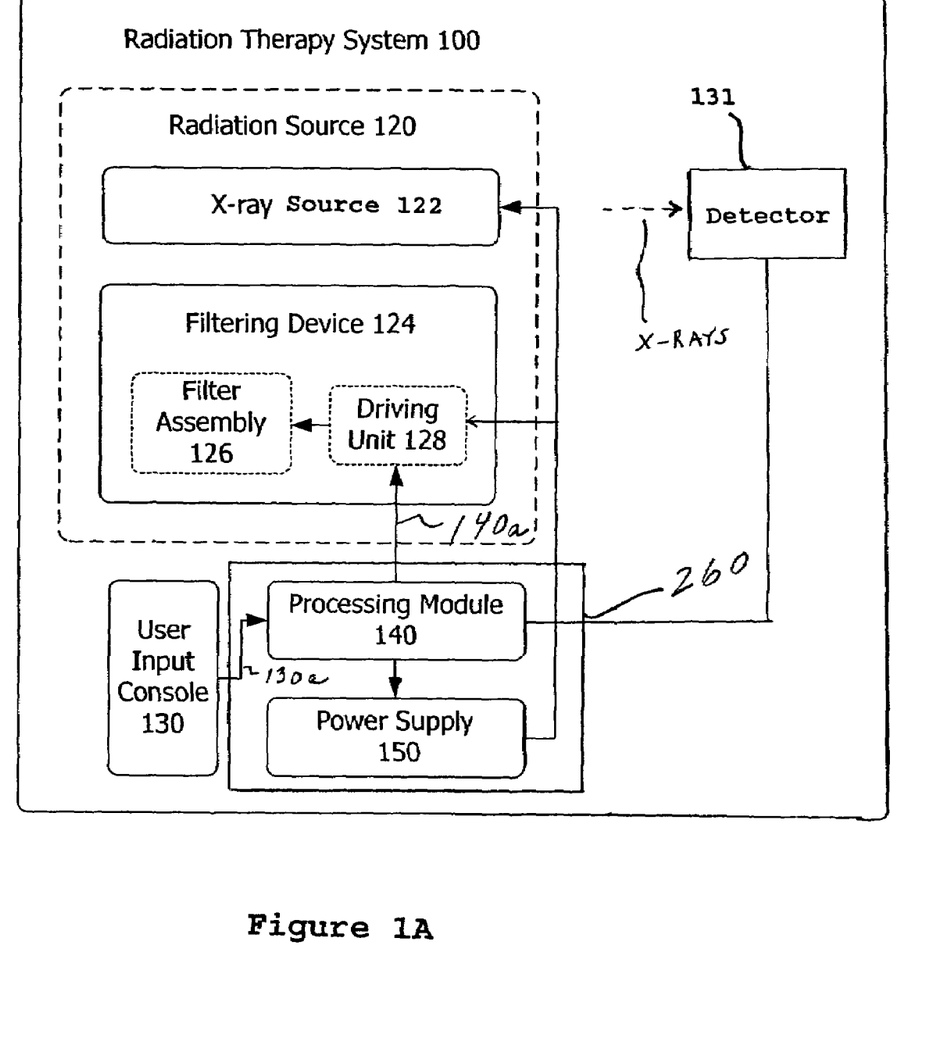
FIG. 1A is a block diagram of a radiation therapy system according to the present invention.

FIG. 1A: The Basic Invention

FIG. 1A shows a radiation system 100 according to the present invention, having a radiation source 120 for providing radiation for treating a patient (not shown), including treating skin cancer, wherein the radiation source 120 features an X-ray source 122, a filtering device 124 that changes its filtering characteristic for filtering the radiation for treating the patient in response to a control signal 140a. The whole thrust of the invention is to allow an operator of the radiation therapy system 100 to set and/or change automatically the filtering characteristic or setting without manually handling any filtering assembly or filters 126 in the radiation system 100. In the preferred embodiment shown and described herein below, the filtering characteristic is set and/or changed by rotating the filtering assembly 126.

Moreover, the radiation source 120 also includes an X-ray tube or source that provides X-rays for treating the patient. X-ray tubes or sources are known in the art and the scope of the invention is not intended to be limited to any particular type or kind thereof either now known or later developed in the future. The filtering device 124 includes the filter assembly 126 and a driving unit 128 for rotating the same. In operation, the driving unit 128 responses to the control signal from a processing module 140 (See also FIG. 5). The radiation therapy system also includes a user input console 130 (See also FIG. 5) for receiving user or operator inputs, the processing module 140 for processing the same, and a power supply or generator 150 for powering the overall system 100.

The radiation therapy system may also include a detector 131 that responds to x-rays from the x-ray source and provides a detector signal containing information about the same. The processing module 140 responds to the detector signal, processes the same and provides information about the x-rays being detected. In operation, before treating a patient, the radiation therapy system 100 may be tested by coupling the detector 131 to the radiation source 120 on, for example, a x-ray window or port 224 shown in FIGS. 1B, 2A and 2B. In this case, the information about the x-rays from the processing module 140 may provide an indication about the radiation output of the system 100 before treating the patient. X-ray detectors are known in the art, and the scope of the invention is not intended to be limited to any particular type or kind thereof either now known or later developed in the future.

Figure 1B:
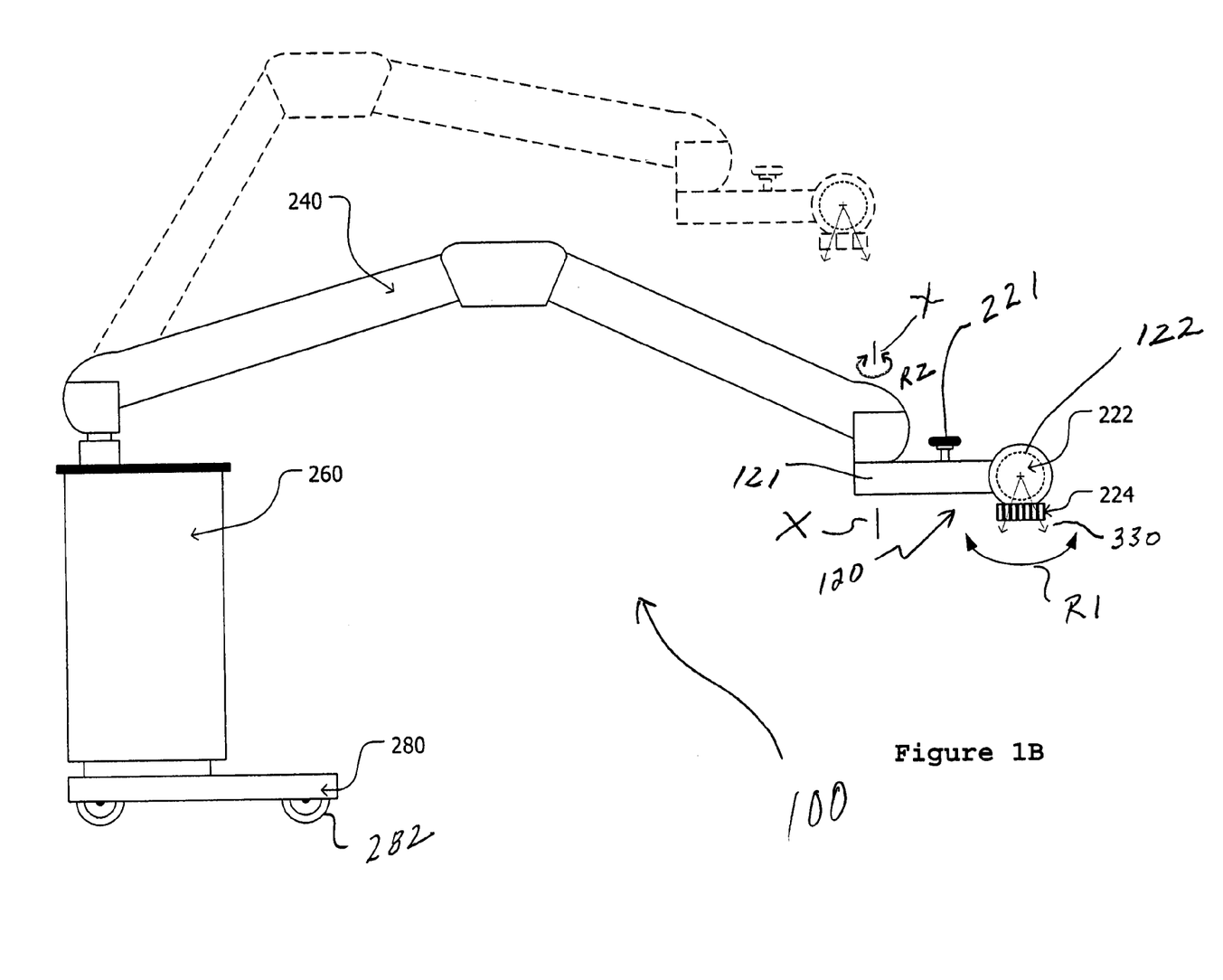
FIG. 1B is a schematic drawing of a radiation therapy system according to the present invention.

FIG. 1B

FIG. 1B shows one embodiment of the radiation therapy system 100, which includes a housing unit 260 arranged on a base 280 having optional wheels 282 for moving the same. The housing unit 260 may contain, among other things, the power supply 150 and the processing module 140, as shown in FIG. 1A. The system 100 also includes an adjustable or cantilever arm 240 having the radiation source generally indicated as 120 attached to the end thereof. The radiation source 120 has an X-ray source 122 arranged therein, and may also includes a handle 221 for placing the radiation source 120 at different heights and angles in relation to the patient. The radiation source 120 is rotatable as indicated by the arrow R1. FIG. 1B shows an X-ray tube focal spot generally indicated as 222, where the X-rays from the X-ray source 122 are focused, consistent with that described below.

The radiation source 120 also has the X-ray window or port 224 for providing the x-rays to the skin of the patient.

The radiation source 120 may also be rotatable on an arm 121 about an axis X as shown by an arrow indicated by the reference label R2 for arranging the radiation source in relation to the patient.

Figure 2A:
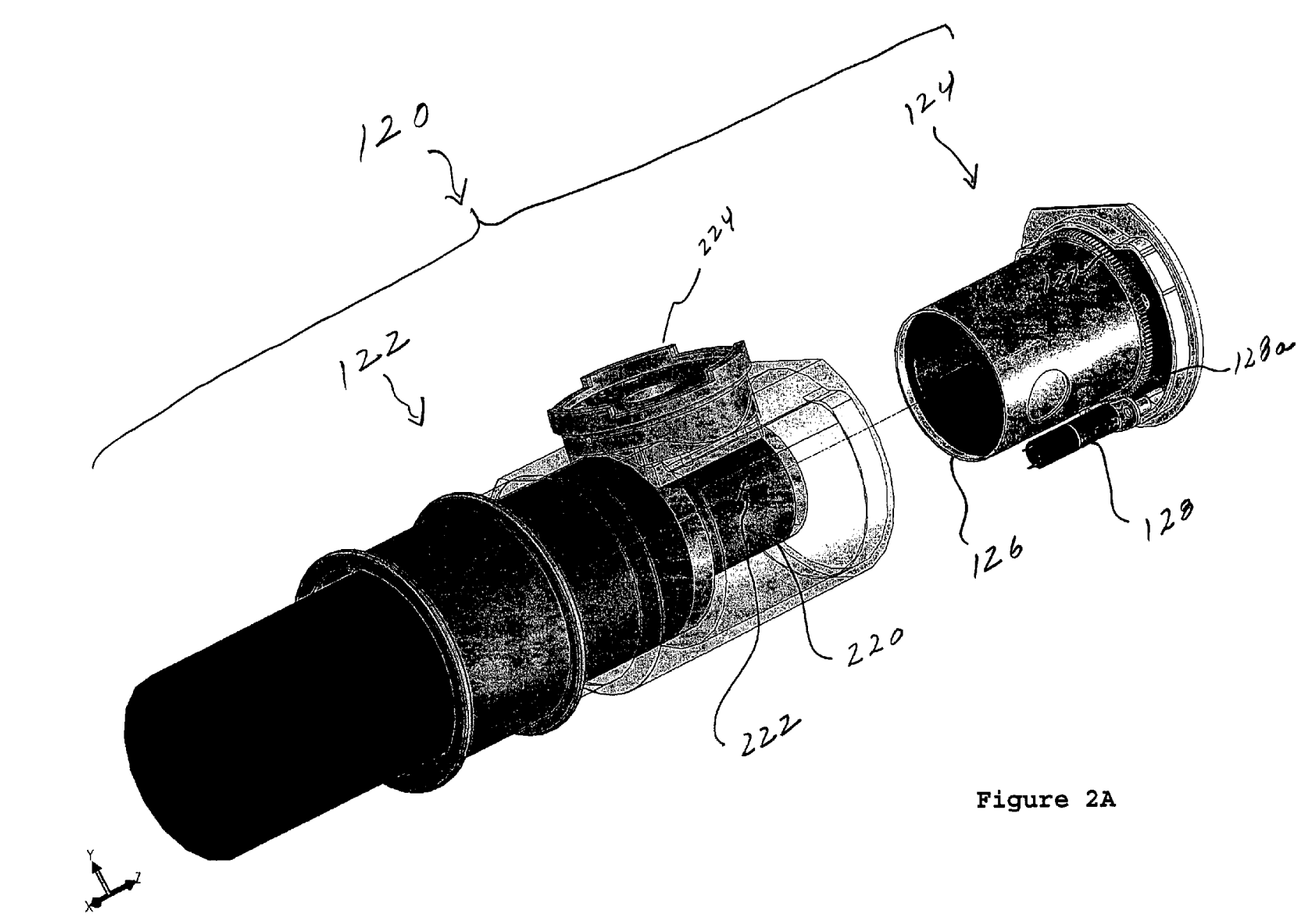
FIGS. 2A and 2B are partial exploded perspective views of the radiation source 120 shown in FIGS. 1a and 1B according to the present invention.
Figure 2B:
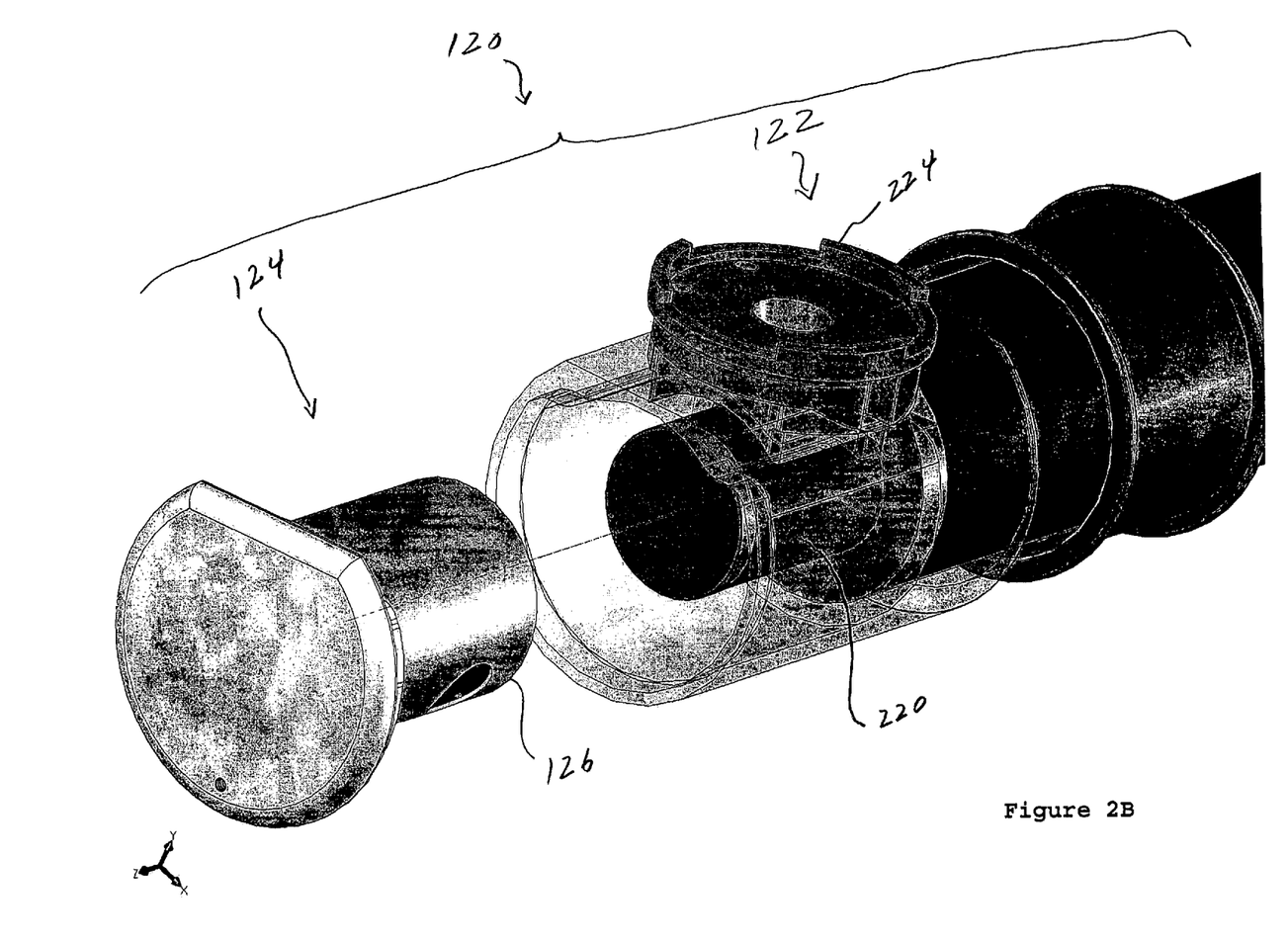

FIGS. 2A and 2B

FIGS. 2A and 2B show partial exploded perspective views of the basic components of the radiation source 120 (FIGS. 1A and 1B), which includes the X-ray source generally indicated as 122 arranged in relation to the filtering device generally indicated as 124 with other corresponding features indicated by reference labels consistent with that shown in FIGS. 1A and 1B.

As shown, the X-ray source 122 includes a radiation head or tube 220 that provides the X-rays that are focused at the X-ray tube focal spot 222 (see also FIG. 1B). The radiation head or tube 220 is known in the art, and the scope of the invention is not intended to be limited to any particular type or kind thereof either now known or later developed in the future.

The filtering device 124 includes the rotatable filtering assembly 126 (see also FIG. 1A) which is rotatable within the radiation source 120 consistent with that described below.

Figure 2C:
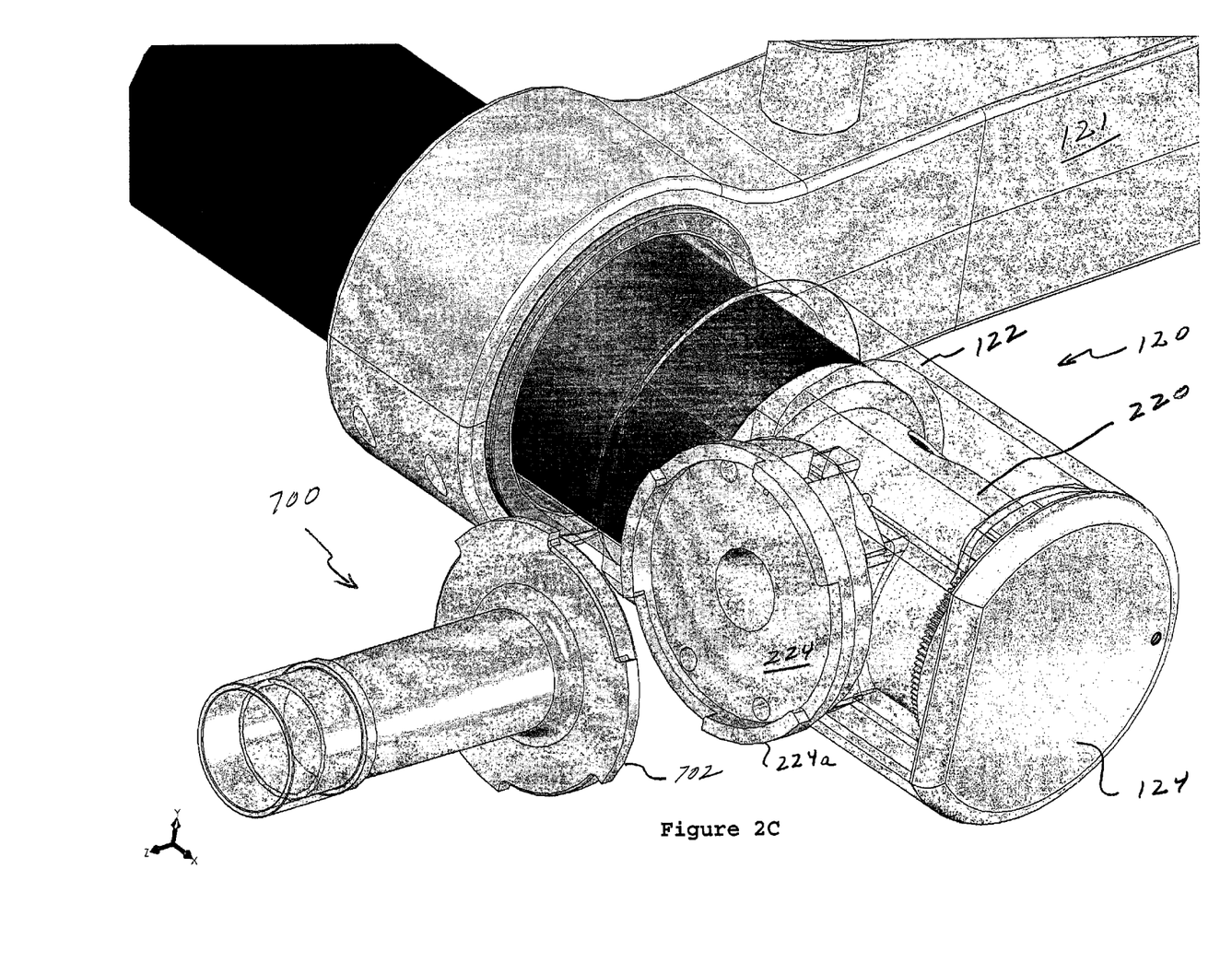
FIG. 2C shows a perspective exploded view of an applicator arranged in relation to the radiation source 120.

FIG. 2C shows an applicator 700 having an end 702 for coupling into a corresponding end 224a of the x-ray window or port 224 and providing the x-rays to the skin of the patient.

Figure 2D:
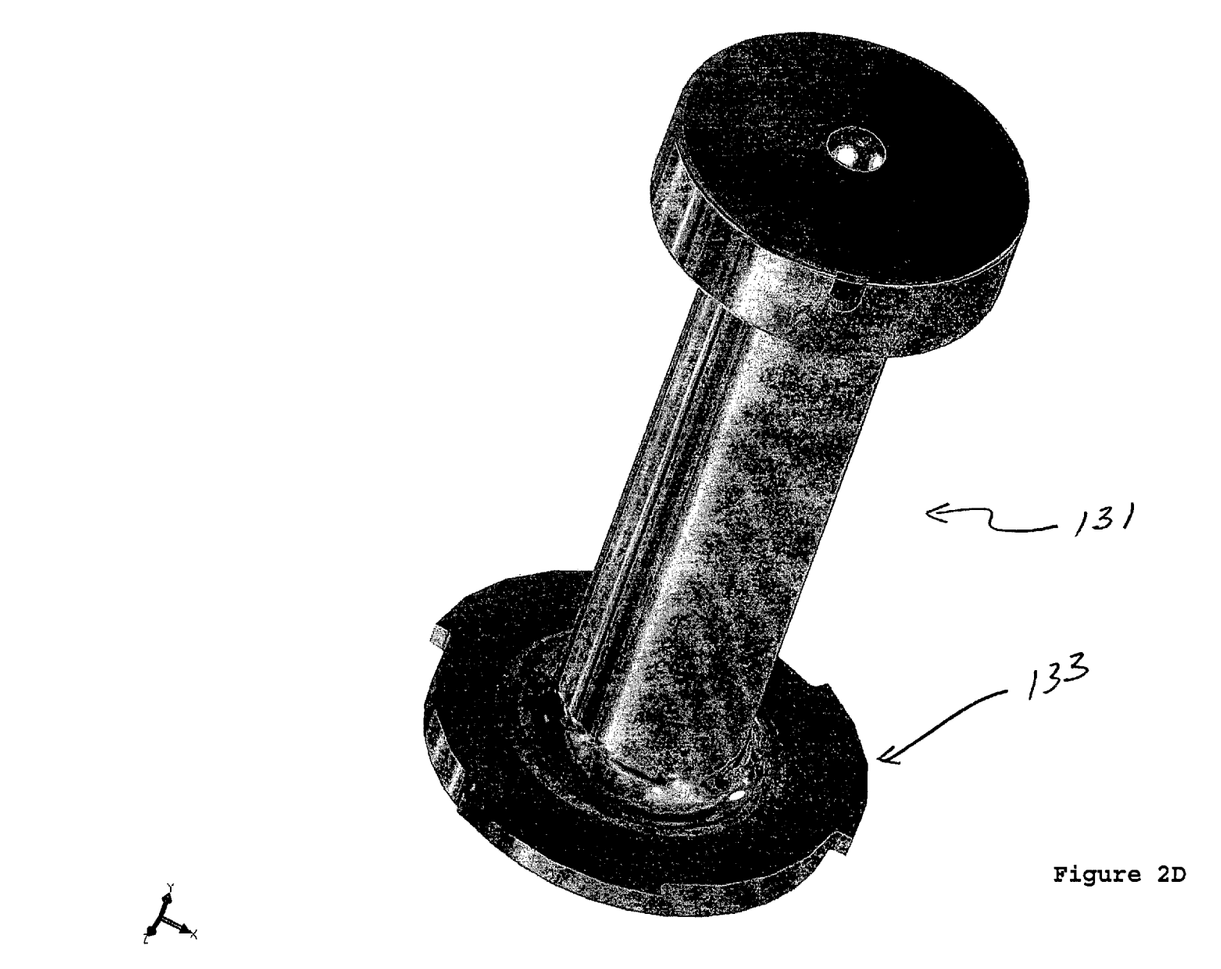
FIG. 2D shows a perspective view of a detector shown in FIG. 1A.

FIG. 2D shows the detector 131 having an end 133 for coupling into the corresponding end 224a of the x-ray window or port 224. The wire for coupling the detector 131 to the module 140 (FIG. 1A is not shown.

FIG. 3: The Filtering Device 124

Figure 3A:
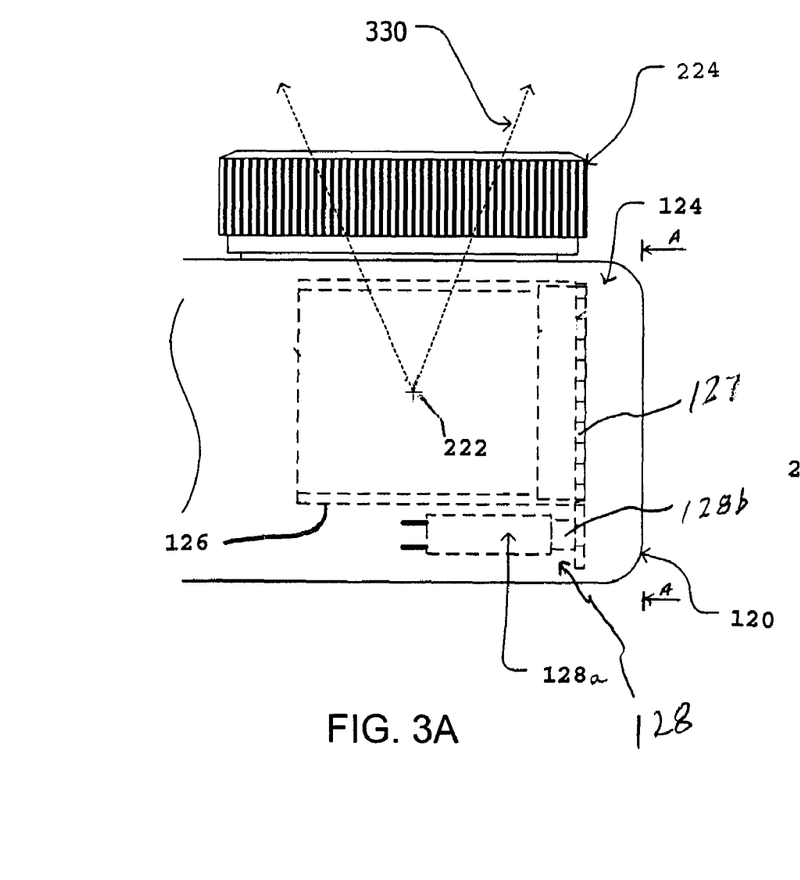
Figure 3B:
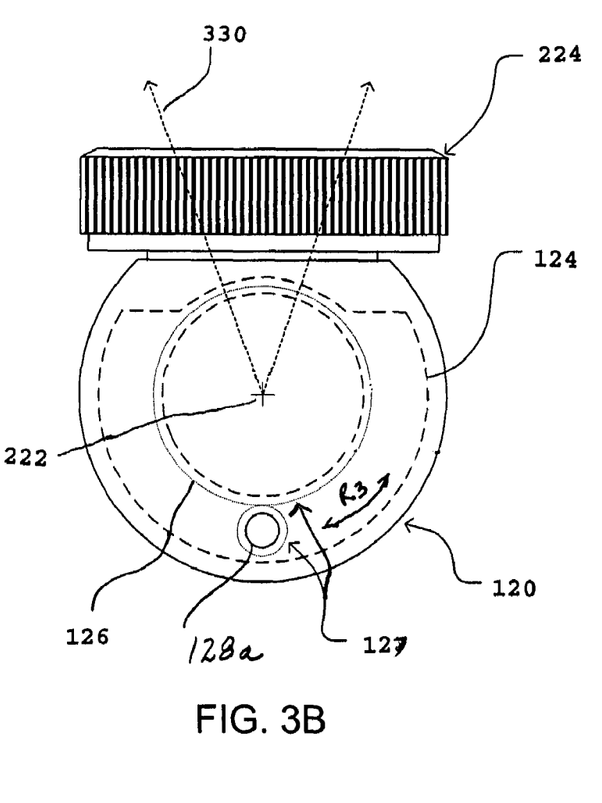
FIG. 3B is a view along lines A-A of the radiation source shown in FIG. 3A.

FIGS. 3A and 3B show a partial view of the radiation source 120 in greater detail, including the filtering device 124, the filter assembly 126 and the driving unit 128. The filter assembly 126 is shown as a rotatable cylinder with the focal point 222 of the X-ray source 122 (see FIGS. 1A and 2A to 2C) located inside the same that rotates around the x-ray source 122 along the path of arrow R3. The filtering assembly 126 encircles the focal point 222 of the radiation head or tube 220 (see FIGS. 2A and 2B) and is rotated by the driving unit 128 in response to the control signal from the processing module 140 (FIG. 1A). The X-rays 330 emitted from the radiation head or tube 220 (see FIGS. 2A and 2B) pass through the filtering assembly 126 and exits through the x-ray window or port 224 for treating the patient.

The driving unit 128 may take the form of a DC motor 128a having a gearing arrangement 128b for coupling to a corresponding gearing arrangement 127 on a filtering assembly 126 for rotating the same. Such motor and gearing arrangements are known in the art, and the scope of the invention is not intended to be limited to any particular type or kind either now known or later developed in the future.

FIG. 4

Figure 4A:
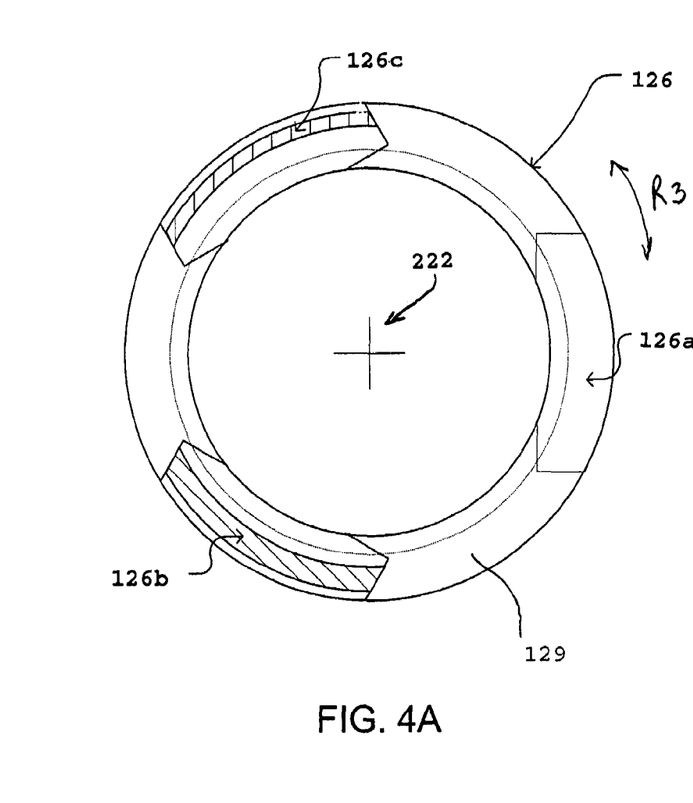
Figure 4B:
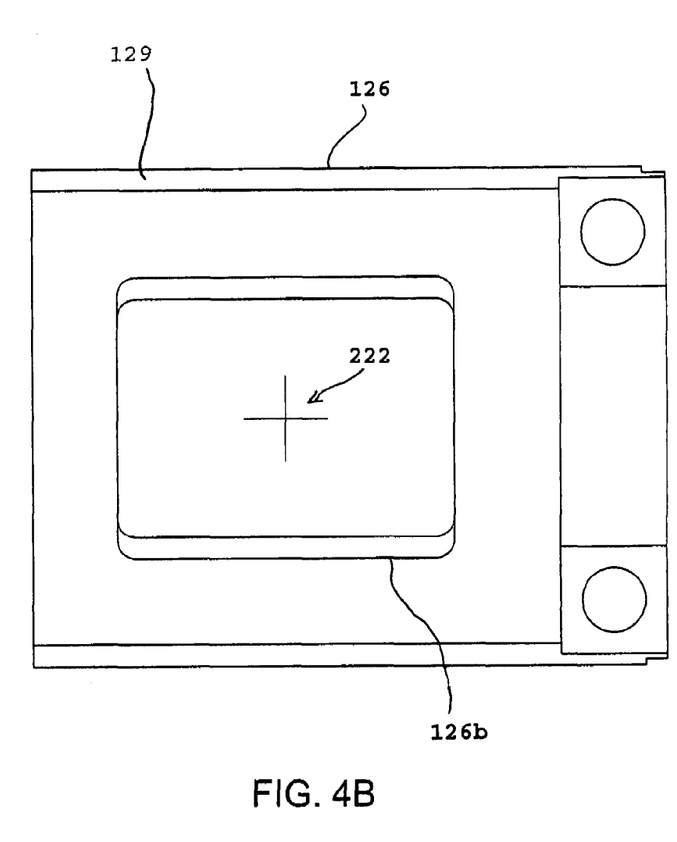
FIG. 4B is a side view of the rotatable filter shown in FIG. 4A through filtering medium 126b.

FIGS. 4A and 4B show the filtering assembly 126 that includes a member 129 having various filtering medium 126a, 126b, 126c circumferentially arranged therein or thereon, including a radiation blocker 126a and two filters 126b and 126c. In operation, the member 129 rotated as indicated by arrow R3 for arranging a filtering medium 126a, 126b, 126c between the X-ray tube focal point 222 and the skin of the patient for filtering or blocking the X-rays. The member 129 is shown by way of example as a cylinder, although the scope of the invention is not intended to be limited to any particular geometric shape thereof. Embodiments are envisioned in which the member 129 takes the form of another geometric shape such as a cube having four side with suitable filtering medium arranged therein or thereon. The radiation blocker 126a may take the form of a lead or other suitable material for blocking radiation either now known or later developed in the future. The radiation blocker 126a is set when the system 100 is used during the warm-up mode. The two filters 126b, 126c may take the form of a medium or material for filtering radiation, such as aluminum or other suitable material for filtering radiation either now known or later developed in the future. For instance, in one particular embodiment 0.75 mm of aluminum and 1.10 mm of aluminum is used for filtering 70 and 100 Kv of radiation. It is important to note that the scope of the invention is not intended to be limited to the type or kind of medium or material being arranged in the filtering assembly 126, the thickness of the medium or material, the number of filters for doing the same, or the type or kind of radiation being filtered. For example, embodiments are envisioned using a different number of filters such as one filter or three filters, etc., for filtering radiation other than, or in addition to, the radiation at 70 and 100 Kv set forth above.

Figure 5:
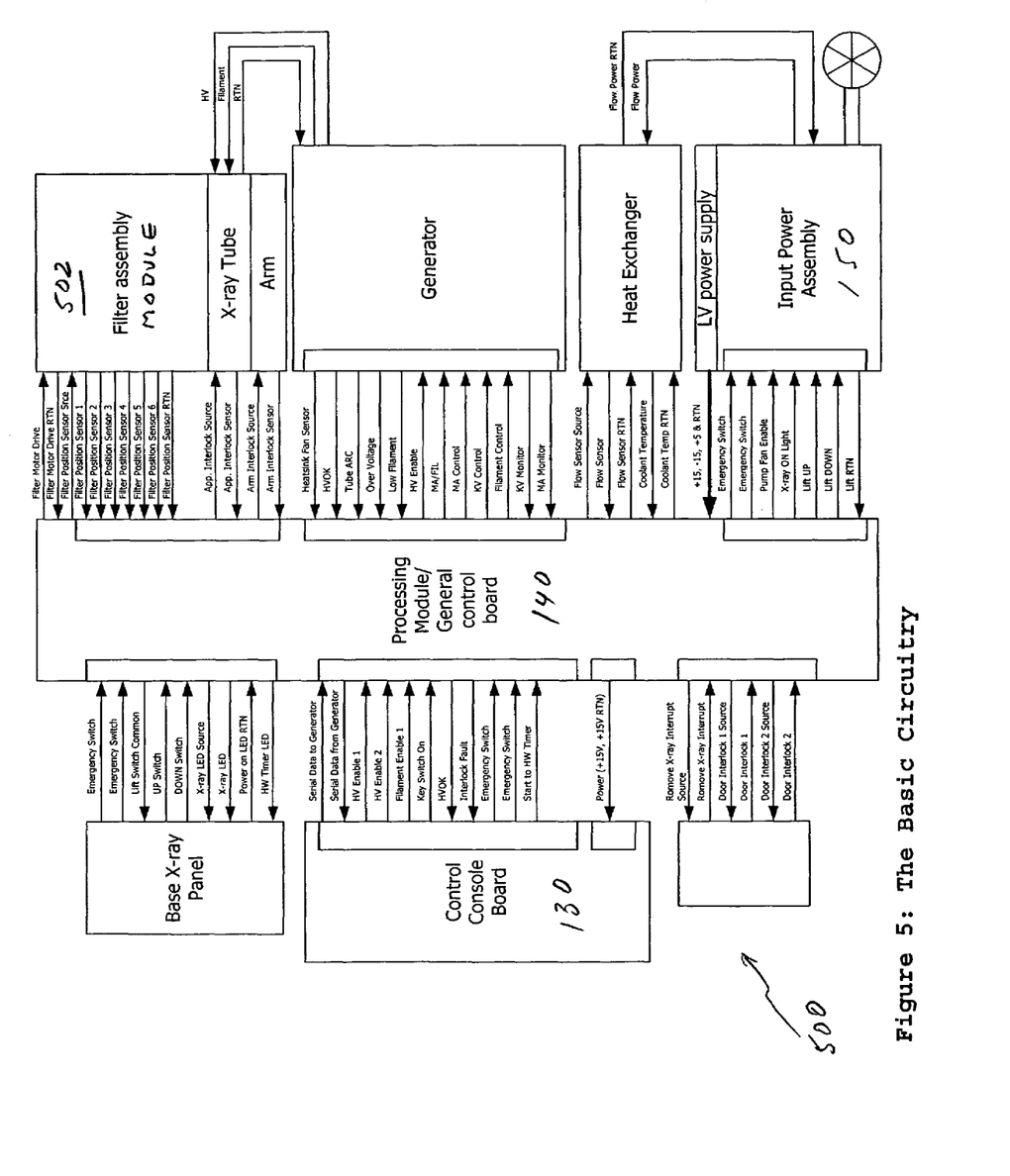
FIG. 5 is a detailed block diagram of a radiation therapy system according to current invention.

FIG. 5: The Circuitry 500

FIG. 5 shows a diagram of circuitry generally indicated as 500 for implementing the present invention. The circuitry 500 includes a filtering assembly module 502 for implementing the functionality of changing the filtering characteristic of the filter assembly 126 (see FIG. 1A) for filtering the radiation for treating the patient in response to a control signal 140a (FIG. 1A). As shown, filtering assembly module 502 receives a filter motor drive signal and a filter position sensor signal from the processing module/general control board 140, and provides a filter motor drive signal for driving the driving unit 128 ((see FIG. 1A)), as well as one or more filter position sensor signals, to the processing module/general control board 140.

The User Input and Processing Modules 130, 140

The functionality of the modules 130 or 140 shown in FIG. 1A may be implemented using hardware, software, firmware, or a combination thereof. In a typical software implementation, the modules 130 and 140 would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology either now known or later developed in the future. The modules 130 and 140 are also shown in relation to other elements of circuitry 500, as discussed below.

The Other Elements

The other elements in the circuitry 500 including the base X-ray panel, the generator, the heat exchanger, input power assembly are shown by way of example, but do not form part of the thrust of the underlying invention.

Figure 6:
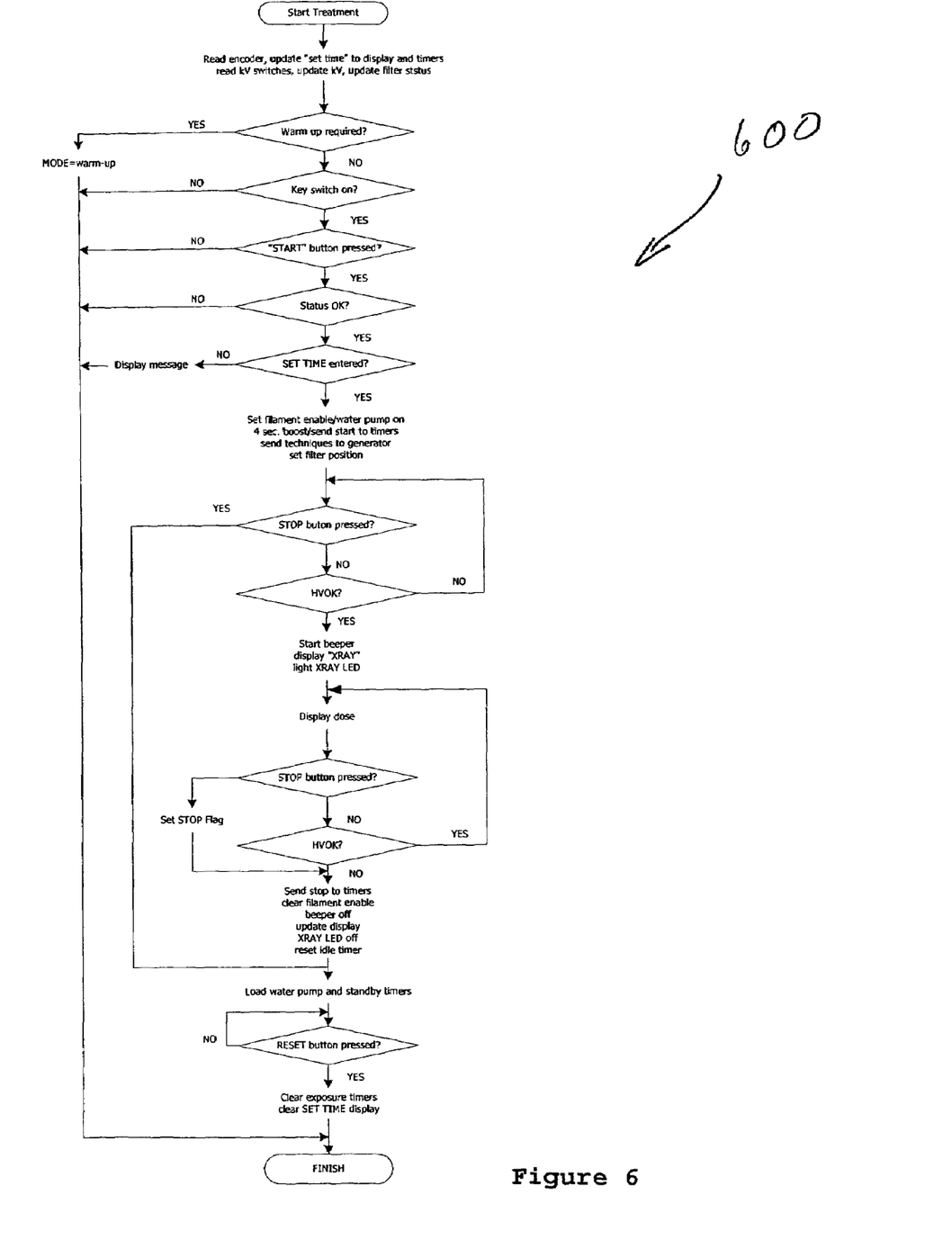
FIG. 6 is a flow chart of controlling mechanism of a radiation therapy system according to current invention.

FIG. 6: The Flowchart 600

FIG. 6 shows a flowchart generally indicated as 600 for implementing a method according to the present invention. The flowchart in FIG. 6 is shown, by way of example only, for a typical flow diagram of a radiation therapy session. At the beginning of the session, the system 100 is initialized. It checks whether a warm-up is required (if the system power is off initially). If a warm-up is needed, the system 100 proceeds with warm-up procedure with the radiation blocker 126a in place of the filters 126b, 126c to prevent x-ray from leaking out.

If the system 100 has already warmed up, a therapy session can start. In this case, the operator, via the input console 130 (FIGS. 1A and 5) selects a x-ray tube voltage and current combination from a list of available settings, and sets an exposure time. The central processing module 140 (FIGS. 1A and 5) sends a signal to the driving unit 128 (FIGS. 1A and 3) that places the selected filter 126b, 126c for that setting in the position between the x-ray tube 220 (FIG. 2) and the object to be irradiated.

For calibrating x-ray dose, before each treatment the integral x-ray detector assembly is inserted into the x-ray port. A short exposure (10 sec) is made and the radiation detector assembly measures the radiation output of the superficial radiation treatment system. The value of radiation output (a voltage level signal) is compared to the value expected for the technique factors of the treatment station and the operator is notified of the result on the information screen of the control console.

It is important to note that the scope of the invention is not intended to be limited to performing the method according to the steps set forth in FIG. 6, because embodiments are envisioned using other sequences of steps for implementing the same.

Figure 7:
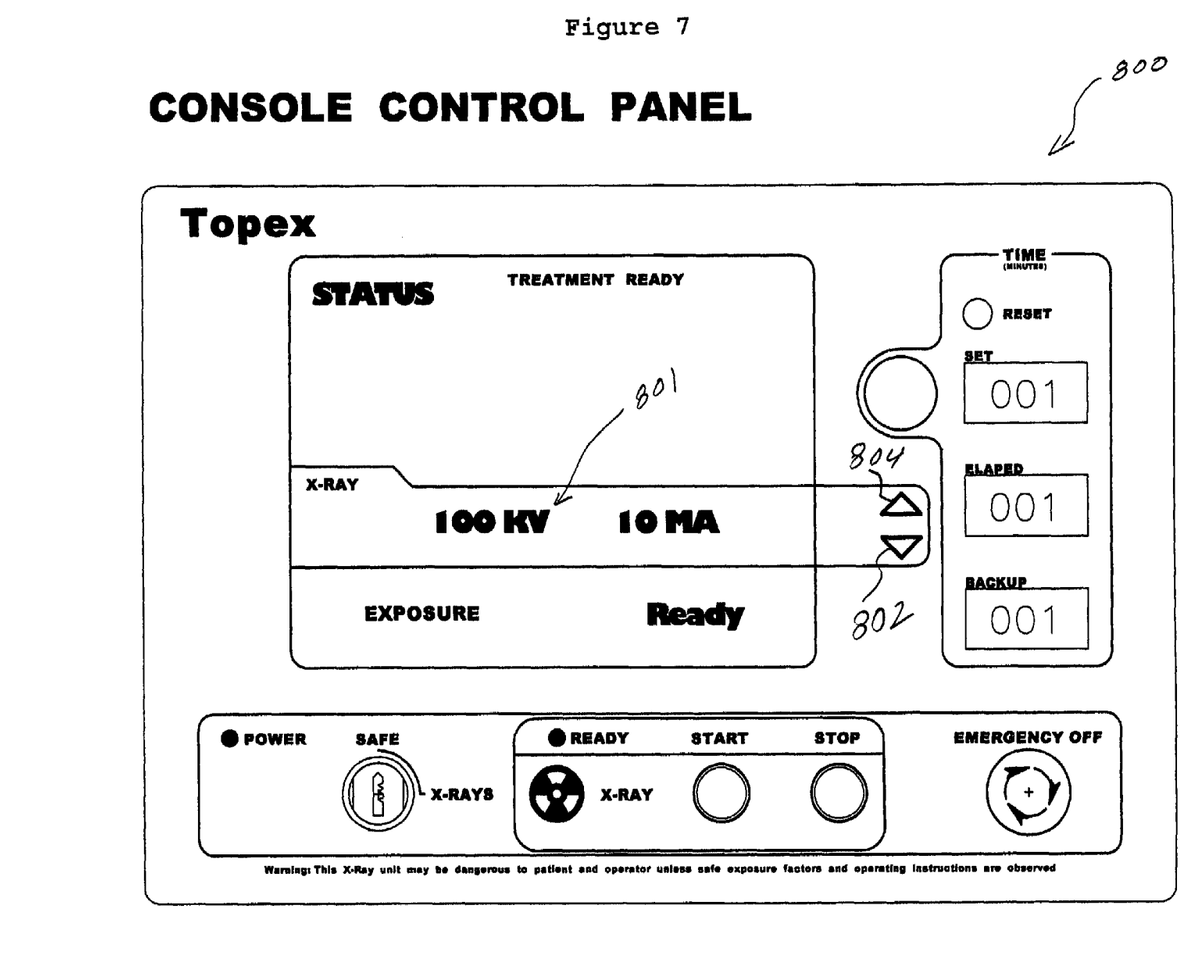
FIG. 7 shows a console control panel of the user input console shown in FIG. 1 for receiving the operator input for the system 100 shown in FIG. 1.

FIG. 7: The Console Control Panel

FIG. 7 shows a console control panel generally indicated as 800 for receiving operator inputs for controlling the radiation therapy system 100. In response to one or more of the operator inputs, the user input console module 130 (FIG. 1A) provides a user input console module signal 130a for controlling operator input functionality of the radiation therapy system 100. For example, in order to provide and/or change a KV setting indicated by 801 for treating a patient, the user pushes the up or down arrows 802, 804. In response, the user input console module 130 (FIG. 1A) provides the user input console module signal 130*a* to the processing module 140 with information about the KV setting. In response, the processing module 140 provides the processing module signal 140*a* to the driving unit 128, which causes the motor 128*a* (see FIGS. 3A and 3B) to rotate the filter assembly 126 so as to change its filtering characteristic for filtering the radiation for treating the patient.

The console control panel 800 also has keys or inputs for controlling other operator input functionality of the radiation therapy system 100, including but not limited to start, stop, and emergency shutoff functionality. The console control panel 800 also has various lights or LEDs for providing one or more indications of various times, including set, elapsed and backup, as well as power on/off and ready.

Other Possible Embodiments

The scope of the invention is not intended to be limited to only rotating the filtering assembly 126 to change the filtering characteristic. For example, other embodiments are envisioned in which the filtering device may include filters 126*b*, 126*c* and/or a radiation blocker 126*a* that are linearly arranged on the filter assembly 126 in combination with an alternative driving unit or arrangement for linearly translating the filtering assembly in response to a control signal such as signal 140*a* in order to change its filtering characteristic. Moreover still, an embodiment is envisioned in which the filtering assembly may include a filtering medium that responses to the control signal in order to change its filtering characteristic, for example, by changing the density of the filtering medium or other suitable characteristic thereof.

The present invention is also intended to include a radiation system having a radiation source for providing radiation for treating an object or workpiece, instead of a human patient, featuring such an aforementioned filtering device and rotatable filtering assembly that changes its filtering characteristic for filtering the radiation in response to such a control signal.

The Scope of the Invention

It should be understood that, unless stated otherwise herein, any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein without departing from the spirit and scope of the present invention.

What is claimed is:

1. A radiation therapy system having a radiation source for providing radiation for treating a patient, including treating skin cancer, characterized in that
the radiation source comprises a filtering device having a plurality of filters, each with different filtering characteristics for filtering the radiation for treating the patient with one of the plurality of filtering characteristics, a focal point of the radiation source being located in the center of the filtering device and encompassed by the filtering device, the filtering device configured to rotate about the focal point to change the filtering characteristics in response to a control signal.

2. A radiation therapy system according to claim 1, wherein the filtering device includes a filtering assembly having a cylindrical member with the plurality of filters circumferentially arranged thereon.

3. A radiation therapy system according to claim 2, wherein the filtering device includes a driving unit configured to rotate the filtering assembly about the focal point in response to the control signal in order to change its filtering characteristic.

4. A radiation therapy system according to claim 3, wherein the driving unit includes a motor having a gearing arrangement configured to couple to or with a corresponding gearing arrangement on a filtering assembly of the filtering device configured to rotate the same.

5. A radiation therapy system according to claim 4, wherein the radiation source includes an X-ray source configured to provide the radiation.

6. A radiation therapy system according to claim 2, wherein the filtering assembly includes at least one filter, a radiation blocker or some combination thereof.

7. A radiation therapy system according to claim 1, wherein the radiation therapy system also comprises a processing module configured to respond to an input provided by a user and provide the control signal for changing filtering characteristics.

8. A radiation therapy system according to claim 7, wherein the input provided by the user contains information that is used to determine a filter setting.

9. A radiation therapy system according to claim 7, wherein the radiation therapy system further includes a user input console configured to receive the input provided by the user.

10. A radiation therapy system according to claim 2, wherein the filtering assembly includes at least one filtering medium that responds to the control signal in order to change its filtering characteristic.

11. A radiation therapy system according to claim 10, wherein the density of the filtering medium is changed in order to change its filtering characteristic.

12. A radiation therapy system according to claim 1, wherein the radiation therapy system also includes a detector configured to respond to x-rays from the radiation source and provide a detector signal containing information about the same.

13. A radiation therapy system according to claim 12, wherein the radiation therapy system also includes a processing module configured to respond to the detector signal, process the same and provide information about the x-rays being detected, including an indication about the radiation output of the system before treating the patient.

14. A system having a radiation source for providing radiation in relation to an object, characterized in that
the radiation source comprises a filtering device having a plurality of filters, each with different filtering characteristic for filtering the radiation for treating the patient with one of the plurality of filtering characteristics, a focal point of the radiation source being located in the center of the filtering device and encompassed by the filtering device, the filtering device configured to rotate about the focal point to change the filtering characteristics in response to a control signal.

15. A radiation therapy system according to claim 14, wherein the filtering device includes a driving unit configured to rotate a filtering assembly having one or more filters in response to the control signal in order to change its filtering characteristic.

16. A method for treating skin cancer of a patient with a radiation therapy system having a radiation source for providing radiation, comprising:

locating a focal point of the radiation source in the center of a filtering device, the filtering device encompassing the focal point of the radiation source and having a plurality of filters, each with different filtering characteristics, for filtering the radiation for treating the patient with one of the plurality configured to filter; and rotating the filtering device about the focal point to change the filtering characteristic of the filtering device in response to a control signal.

17. A method according to claim 16, wherein the step of rotating includes rotating the filtering device which comprises a cylindrical member having a plurality of filters circumferentially arranged thereon.

* * * * *